(12) United States Patent
Gong

(10) Patent No.: US 11,577,039 B2
(45) Date of Patent: Feb. 14, 2023

(54) REPLACEABLE CUSHION FOR RESPIRATORY MASKS

(71) Applicant: Sleepnet Corporation, Hampton, NH (US)

(72) Inventor: Jia Jie Gong, Andover, MA (US)

(73) Assignee: Sleepnet Corporation, Hampton, NH (US)

( * ) Notice: Subject to any disclaimer, the term of this patent is extended or adjusted under 35 U.S.C. 154(b) by 651 days.

(21) Appl. No.: 14/487,526

(22) Filed: Sep. 16, 2014

(65) Prior Publication Data

US 2015/0075531 A1 Mar. 19, 2015

Related U.S. Application Data

(60) Provisional application No. 61/878,799, filed on Sep. 17, 2013.

(51) Int. Cl.
*A61M 16/06* (2006.01)
(52) U.S. Cl.
CPC ......... *A61M 16/06* (2013.01); *A61M 16/0683* (2013.01); *A61M 2016/0661* (2013.01); *A61M 2207/00* (2013.01); *Y10T 29/49945* (2015.01)
(58) Field of Classification Search
CPC .............. A61M 16/00; A61M 16/0683; A61M 16/0605; A61M 16/0611; A61M 16/0622; A61M 16/06; A61M 2207/00; A61M 2016/0661; Y10T 29/49945
See application file for complete search history.

(56) References Cited

U.S. PATENT DOCUMENTS

| | | | |
|---|---|---|---|
| 6,196,223 B1* | 3/2001 | Belter | A41D 13/1176 128/205.25 |
| 6,530,373 B1* | 3/2003 | Patron | A61M 16/06 128/205.25 |
| 6,615,832 B1* | 9/2003 | Chen | A62B 18/08 128/206.28 |
| 6,631,718 B1 | 10/2003 | Lovell | |
| 7,210,481 B1* | 5/2007 | Lovell | A61M 16/06 128/205.25 |
| 8,051,855 B2* | 11/2011 | Ho | A61M 16/06 128/206.21 |

(Continued)

OTHER PUBLICATIONS

Fisher & Paykel Healthcare, "FlexiFitTM 432 Full Face Mask", Product Brochure, www.fphcare, P O Box 14 348, Panmure, Auckland 1741, New Zealand.

(Continued)

*Primary Examiner* — Samchuan C Yao
*Assistant Examiner* — Sarah B Lederer
(74) *Attorney, Agent, or Firm* — Pierce Atwood LLP; Kevin M. Farrell; Christopher Baxter

(57) ABSTRACT

A "replaceable cushion system" allows for a cushion frame with an integral cushion (e.g., a gel bladder) to be quickly and easily swapped in and out of a respiratory mask (e.g., a CPAP mask) while maintaining an effective seal via the compression of a gasket. In all of the preferred embodiments, the cushion frame (with an affixed cushion) is removably attached to a mask shell by a press-fit and by associated prongs and notches. The prongs can be located in the mask shell with the notches in the cushion frame, or vice versa.

28 Claims, 15 Drawing Sheets

(56) References Cited

U.S. PATENT DOCUMENTS

| | | | | |
|---|---|---|---|---|
| 8,146,595 B2* | 4/2012 | Sherman | | A61M 16/06 128/206.21 |
| 8,662,079 B2* | 3/2014 | Ho | | A61M 16/0633 128/206.24 |
| 2003/0236015 A1* | 12/2003 | Edirisuriya | | A61M 16/16 439/191 |
| 2004/0221850 A1* | 11/2004 | Ging | | A61M 16/0616 128/207.11 |
| 2006/0042629 A1* | 3/2006 | Geist | | A61M 16/06 128/206.26 |
| 2006/0283452 A1* | 12/2006 | Woodard | | A61M 16/06 128/205.25 |
| 2007/0221227 A1* | 9/2007 | Ho | | A61M 16/0633 128/206.24 |
| 2008/0053446 A1* | 3/2008 | Sleeper | | A61M 16/06 128/205.25 |
| 2008/0178875 A1* | 7/2008 | Henry | | A61M 16/06 128/201.22 |
| 2008/0190432 A1* | 8/2008 | Blochlinger | | A61M 16/0616 128/207.18 |
| 2009/0095301 A1* | 4/2009 | Hitchcock | | A61M 16/06 128/206.21 |
| 2009/0107506 A1* | 4/2009 | Collazo | | A61M 16/06 128/206.21 |
| 2009/0139527 A1* | 6/2009 | Ng | | A61M 16/06 128/206.26 |
| 2010/0065060 A1* | 3/2010 | Ho | | A61M 16/06 128/206.26 |
| 2010/0108072 A1* | 5/2010 | D'Souza | | A61M 16/0683 128/206.24 |
| 2011/0162654 A1 | 7/2011 | Carroll et al. | | |
| 2012/0266886 A1* | 10/2012 | Davidson | | A61M 16/06 128/205.25 |
| 2013/0276790 A1 | 10/2013 | Moulton et al. | | |

OTHER PUBLICATIONS

Koninklijke Philips Electronics N.V., "It's a game changer. Philips Respironics EasyLife nasal mask with Auto Seal", Product Brochure, www.philips.com/easylife, 2011, 1010 Murry Ridge Lane, Murrysville, PA.

* cited by examiner

REPLACEABLE CUSHION FOR RESPIRATORY MASKS

RELATED APPLICATION

This application claims priority to U.S. Provisional Patent Application, Ser. No. 61/878,799, entitled "REPLACEABLE CUSHION FOR RESPIRATORY MASKS," filed Sep. 17, 2013. Applicant claims priority from that application. Applicant also hereby incorporates by reference that application in its entirety.

FIELD OF INVENTION

This invention relates generally to respiratory masks. More particularly, it relates to cushions for respiratory masks, such as continuous positive airway pressure (CPAP) masks.

BACKGROUND OF THE INVENTION

There is a growing need for supplemental respiratory support for patients in the hospital and home environment. Positive pressure ventilation, in which a supply of pressurized air is delivered to the patient's airway, is often used. Positive pressure ventilation has been used to treat respiratory failure, respiratory insufficiency, and sleep apnea. There are a variety of patient interfaces which can be used to provide positive pressure ventilation including masks and nasal cannula. Mask interfaces are available for home and hospital use with many designs including nasal, oronasal (covering the nose and mouth), and full face masks.

CPAP, or continuous positive airway pressure, is a treatment which uses mild air pressure to keep the airways open. CPAP treatment typically is used by people who have breathing problems, such as sleep apnea.

Sleep apnea is a common disorder that causes pauses in breathing or shallow breaths while you sleep. As a result, not enough air reaches your lungs.

In obstructive sleep apnea, the person's airway collapses or is blocked during sleep. When that person tries to breathe, any air that squeezes past the blockage can cause loud snoring. Mild air pressure from CPAP treatment can prevent that person's airway from collapsing or becoming blocked.

CPAP treatment basically involves: a CPAP machine which blows therapeutic air; and a CPAP mask assembly, which receives air from the machine via an interconnecting hose.

CPAP mask assemblies typically comprise a mask shell of rigid or pliable material (e.g., plastic) with a face-contacting cushion (e.g., a gel filled bladder) which is held in place with headgear (e.g., straps). The shell provides the structure for: a headgear connector; straps which can be removably attached to the headgear connector; and a swiveling elbow assembly to which the hose can be attached. The cushion provides a seal against the patient's face creating a cavity around the airway through which positive pressure ventilation can be applied.

Current mask technologies require cleaning and replacement at regular intervals. A problem with some existing CPAP mask technologies is the complex design of replaceable components. This makes it difficult for the end-user to disassemble and reassemble the mask for cleaning and cushion replacement. The complex geometry of the mask also adds to the difficulty of effectively and thoroughly cleaning masks. Because of the difficulty of use of current designs, end-users are less likely to clean the mask sufficiently or to replace required components at necessary intervals. Unfortunately, an un-cleaned mask can result in the development of respiratory infection in the patient.

While some CPAP masks have incorporated methods for disassembly to make cleaning the masks easier, their complexity of the assembly and disassembly contribute to patients' aversion to cleaning their masks. These masks also tend to feature even more complex geometries which are difficult to clean totally without disassembly. Complex surface areas allow for infection-causing bacteria to reside. That potentially makes such products even more hazardous to patients the longer they are used without cleaning.

There have been attempts by different manufacturers to design a CPAP mask which allows for disassembly and removal of the cushion for cleaning and replacement. Applicant believes all prior attempts have resulted in masks which are difficult to use in practical conditions, and often involve a sacrifice in comfort for the wearer. Both of these problems detrimentally reduce the rate of patient compliance.

One example of a CPAP mask which relies on a replaceable cushion is the ResMed Mirage® SoftGel nasal mask disclosed in U.S. patent application Ser. No. 14/736,980, Publication No. 2011/0162654, filed by Carroll et al. The Mirage® mask design includes a hard plastic frame, attached to a removable gel cushion, which snaps into the mask shell. The plastic frame fits into grooves on the mask shell. This arrangement sometimes does not hold the cushion securely, especially when a wearer tosses and turns while sleeping. During such movement, the Mirage® mask cushion can give way when the patient moves, creating a leak between the frame and cushion. Additionally, it is difficult to align the plastic frame with its receiving groove on the cushion, and the frame is difficult to align and secure on the main mask shell. Furthermore, the cushion has a tendency to get pushed off the frame as the frame is secured to the main mask shell. This design also contributes to excessive mask weight, which can lead to reduced patient comfort.

Another invention attempts to increase the ease of cleaning by making the CPAP mask composed of three components: a shell, an internal cushion, and an external supporting cushion. Respironics' EasyLife™ nasal mask features an external cushion which is mounted on a hard shell. This shell is used to compress an outside lip of the cushion against a receiving groove on the main mask shell. This setup apparently is hard to clean extensively. Additionally, if the inner cushion is not seated perfectly along the entirety of the outside lip, pressurized air (fed into the mask) will leak, causing patient discomfort and decreased therapy pressure, especially since the pressure is only delivered to the patient nasally via the internal cushion. The complexity of reassembly of the mask also poses an obstacle to patient compliance for cleaning and replacement.

Another invention which attempts to make use of a replaceable cushion is Fisher & Paykel's Flexfit™ 432 full face mask. This mask incorporates a flexible cushion (i.e., a single ply polymer) which removably fits into a groove on a mask shell. The cushion comes pre-attached (by the manufacturer) to a separable, outer silicone seal. The outer silicone seal foam presents a porous, high-surface-area component of the mask for bacterial growth if the parts are not separated and cleaned regularly since it is not enclosed or integrated into the mask itself. Cleaning of the parts is achieved after separating the cushion from the mask and the seal from the cushion. Reseating the cushion into the shell is difficult while the foam insert is present.

Accordingly, it is a primary object of the present invention to provide a removable cushion assembly, for a CPAP mask, which provides an effective seal between the removable cushion assembly and the receiving mask body.

It is another primary object to provide differently sized cushions affixed to similar cushion frames, and a single CPAP mask body, whereby an end user can obtain a proper cushion fit without having to buy multiple masks.

It is another object, commensurate with the above listed objects, to provide a removable cushion assembly system which can be used in different types of respiratory masks such as soft-shell moldable masks and textile masks.

SUMMARY OF THE INVENTION

Applicant has disclosed a "replaceable cushion system" which allows for a cushion frame with an integral (e.g., glued or fused) face-contacting cushion (e.g., a gel filled bladder) to be quickly and easily swapped in and out of a respiratory mask (e.g., a CPAP mask) shell, while maintaining an effective seal via the compression of a gasket. This combination provides a tight constant seal even during movement during sleep, along with an easy-to-use interface. It also allows for simple attachment or detachment of the replaceable cushion mechanism while retaining effective sealing and comfort properties by having a gel cushion mounted to the mask body.

In a preferred embodiment, the mask shell has prongs which fit into corresponding notches in the cushion frame. The prongs and receiving notches guide the replaceable cushion frame into the mask shell and allow for quick reassembly. Additionally, the prongs and receiving notches interact mechanically to lock the frame (and its affixed cushion) in place.

This system allows for different sized cushions to be provided to an end user with a single mask shell, such as small, medium and large. That ensures a better fit for the end user without having to buy multiple masks before finding the right fit.

DESCRIPTION OF THE DRAWINGS

The above and other objects of the current invention will become more readily understood when the following text is read in conjunction with the accompanying drawings, in which.

DETAILED DESCRIPTION OF THE PREFERRED EMBODIMENTS

Figure 1:
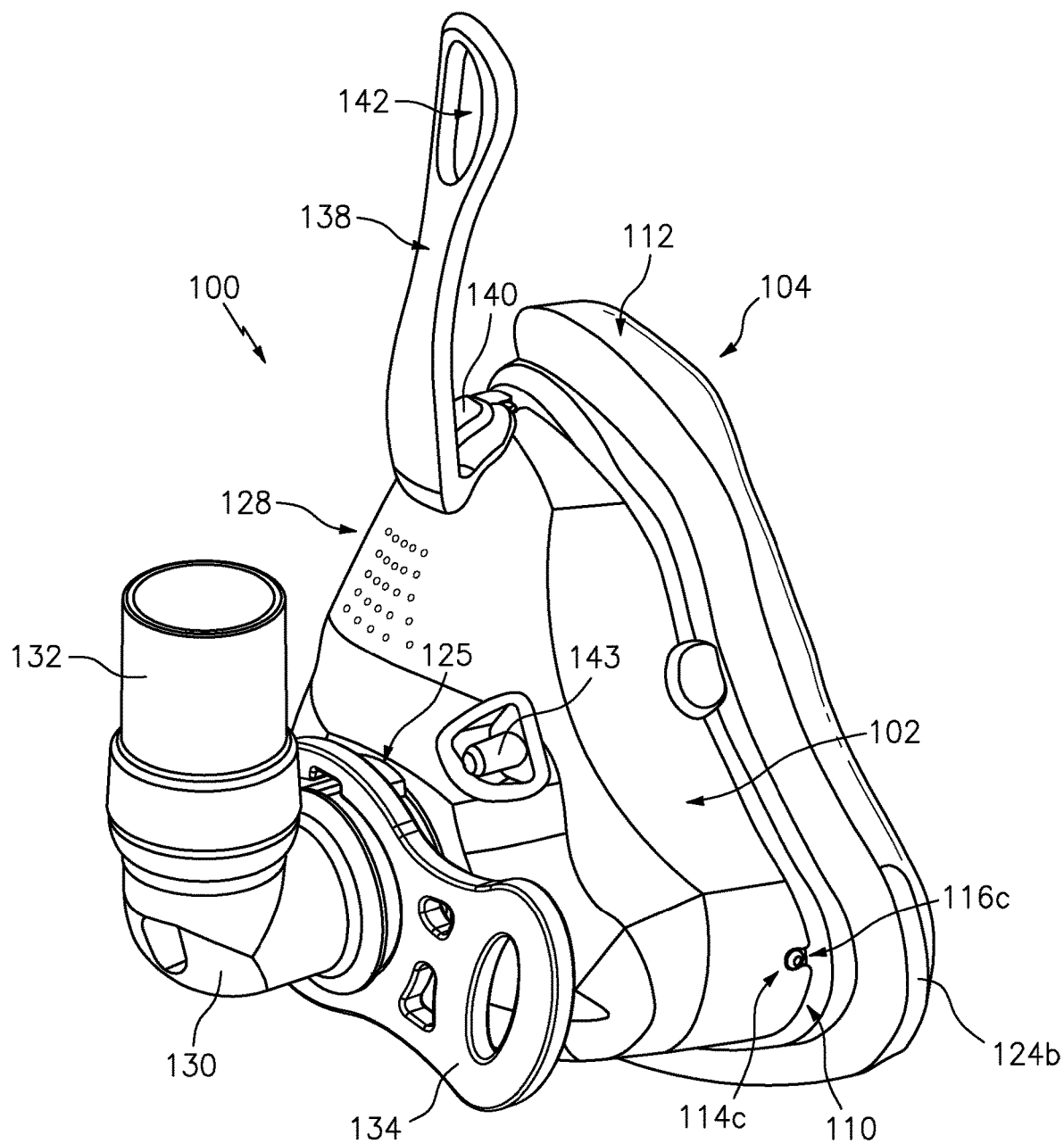
FIG. 1 is a perspective view of a preferred full-face CPAP mask embodiment, constructed in accordance with the present invention, in which a replaceable cushion frame (with an affixed cushion) is removably attached to a mask shell.

Applicant has disclosed a "replaceable cushion system" which allows for a cushion frame with an attached cushion (i.e., a gel or saline filled bladder—hereinafter, "gel bladder") to be quickly and easily swapped in and out of an otherwise standard respiratory mask (e.g., a CPAP mask) shell while maintaining an effective seal via the compression of a gasket. FIGS. 1-7 and 8-12 disclose preferred (alternate) "full-face mask" embodiments 100, 200 of Applicant's invention, while FIGS. 13-14 and 15-16 disclose preferred (alternate) "nasal mask" embodiment 300, 400.

The depicted masks and their components (e.g., headgear connector, gel bladder cushion) are manufactured in the manner described in U.S. Pat. No. 6,631,718 to John R. Lovell, with additions described herein. Sleepnet Corporation is the Assignee of both U.S. Pat. No. 6,631,718 and the present application. Applicant hereby incorporates by reference the entire disclosure of U.S. Pat. No. 6,631,718.

Referring to FIGS. 1-7, Applicant's full-face mask embodiment 100 comprises: a mask shell 102 of a full-face respiratory mask (e.g., the illustrated CPAP mask) 104; a gasket 106 (see FIG. 3) inside and around an end portion of the shell, adjacent a back 108 of the shell 102; and a cushion frame 110, with an integrally attached face-contacting cushion 112, removably nestled inside shell 102.

Figure 2:
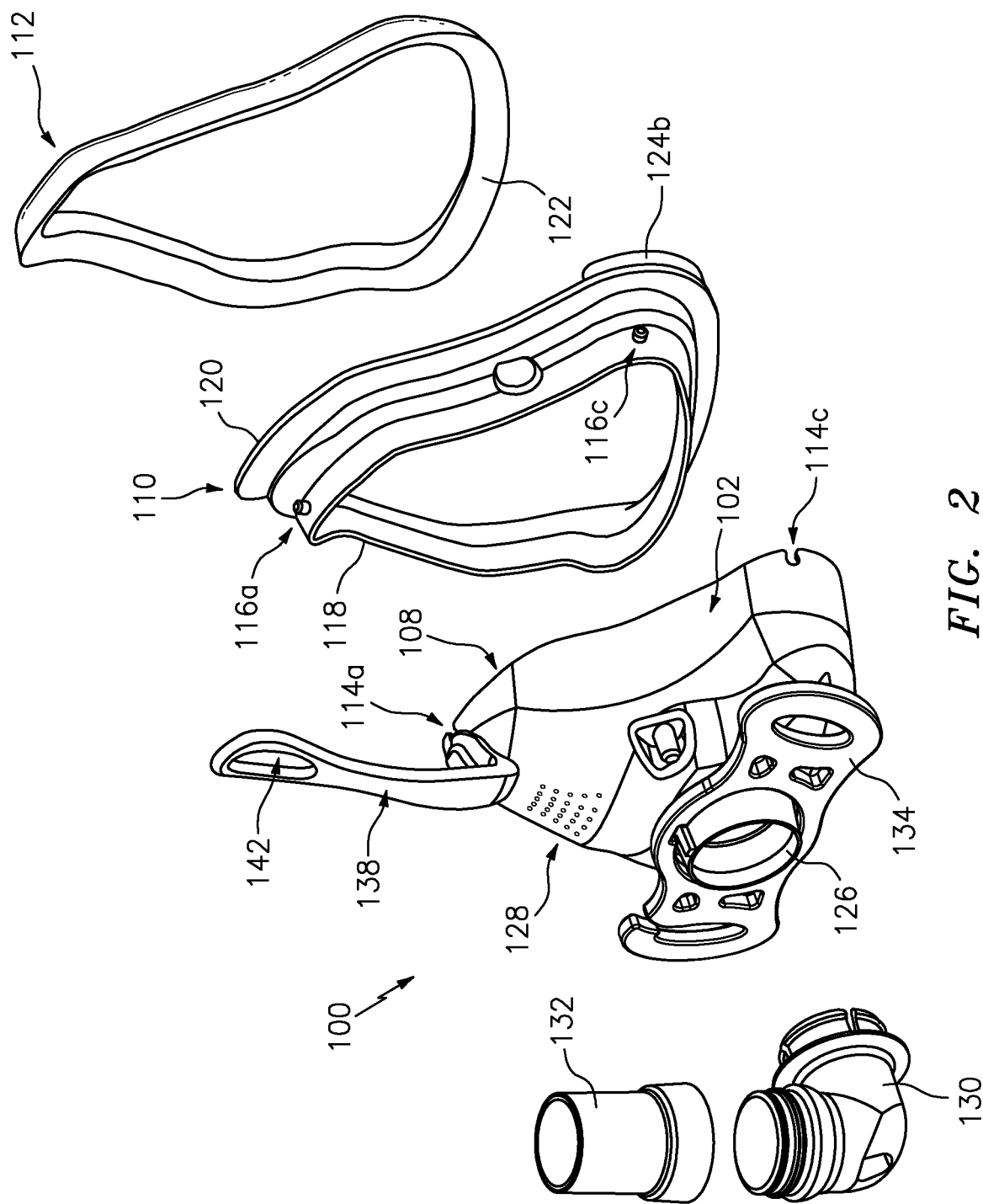
FIG. 2 is a partially exploded perspective view of the CPAP mask showing (among other parts): the mask shell; a replaceable cushion frame; and a cushion.
Figure 3:
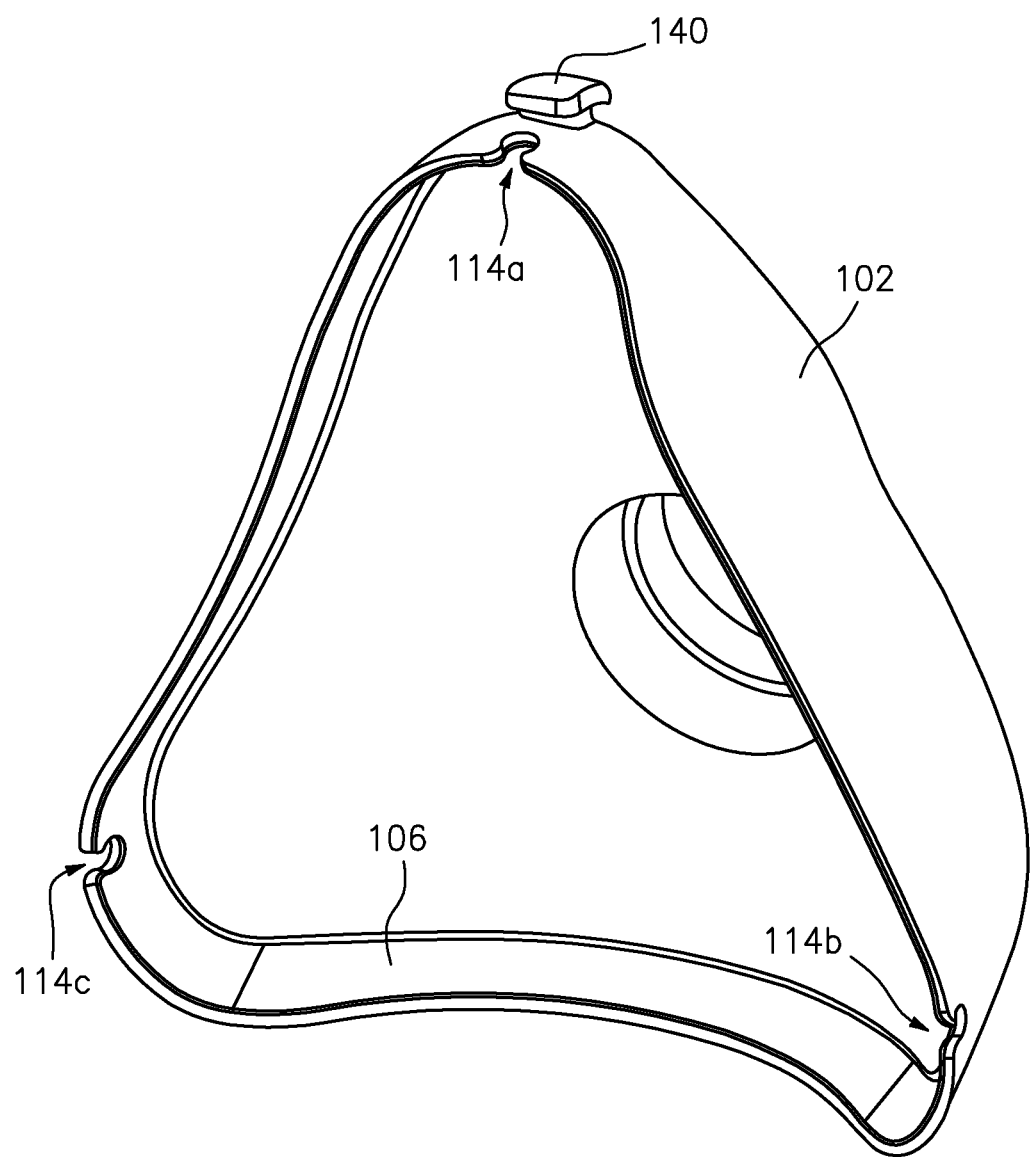
FIG. 3 is a rear perspective view of the mask shell showing: three spaced notches in the shell; and a gasket inside the shell, adjacent its opening and the prongs.

The mask receiving shell 102 also features receiving notches 114a, 114b, 114c spaced around the shell 102 (see, e.g., FIGS. 2-3).

The preferred cushion frame 110 is shown in FIGS. 2, 4-6. Guide prongs 116a (see FIG. 5), 116b, 116c snap into notches 114a, 114b, 114c to secure the cushion frame 110 (and its permanently attached cushion 112) to the mask shell 102. A rim 118, on a front side of the cushion frame 110, is correspondingly shaped like the inside of shell 102 near back 108. Rim 118 is designed to fit seal against the gasket band 106. The gasket 106 preferably is made of a thermoplastic elastomer or thermoplastic polyurethane).

Cushion frame 110 has an annular, flat lip 120 on its opposite or backside. Lip 120 is substantially perpendicular to rim 118. A front (non-face-contacting) portion 122 of the gel cushion 112 preferably is attached to the lip 120, and frame 110, by any suitable adhesive (not shown). Alternatively, a cushion could be fused onto the frame 110, with or without a lip 120.

Two ribs (one shown at 124b) extending outwardly from lip 120. Cushion 112 is also affixed to an inside surface of each rib.

Figure 4:
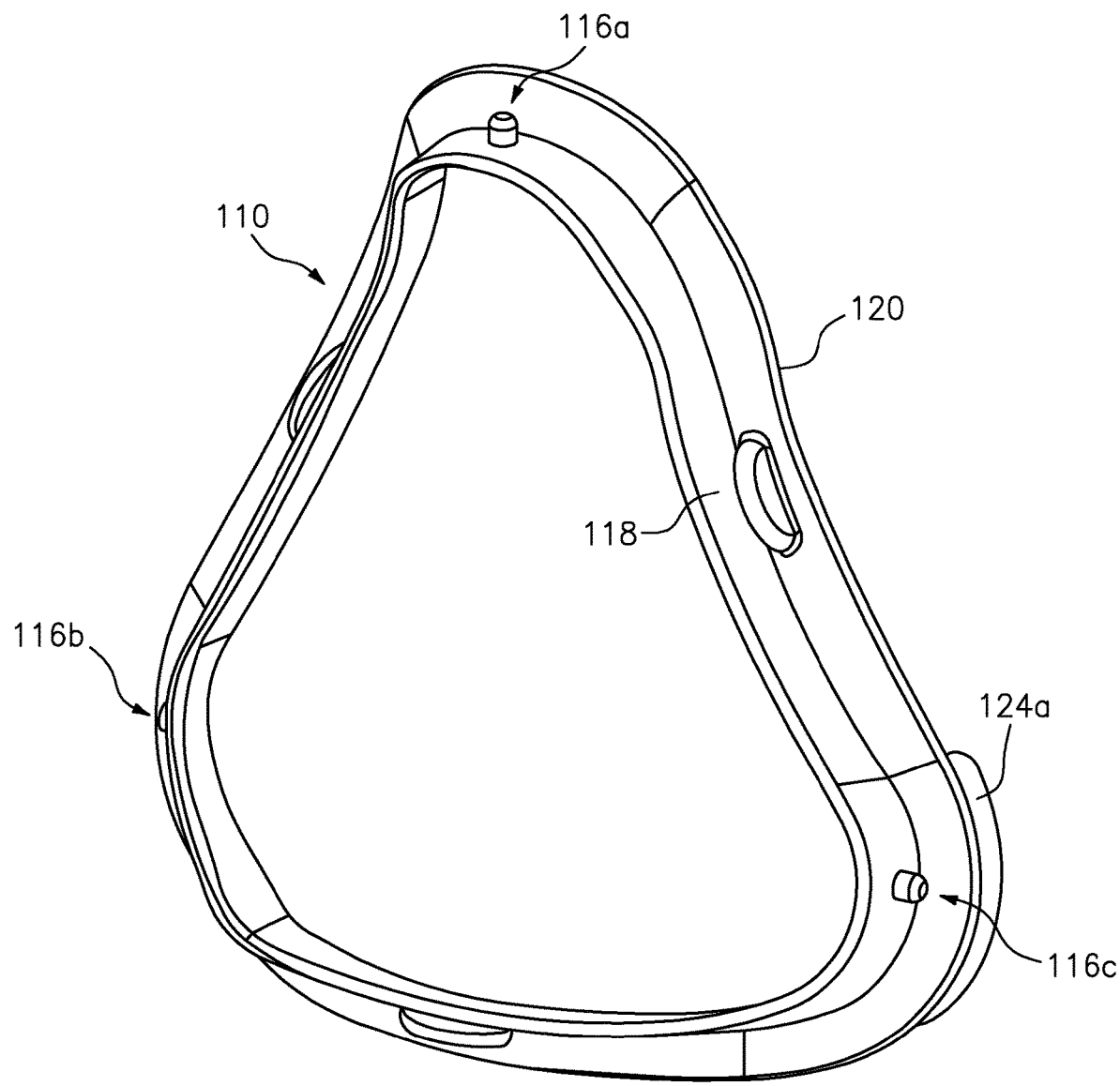
FIG. 4 is a front perspective view of the cushion frame, without a cushion attached, showing a front rim with three spaced prongs.
Figure 5:
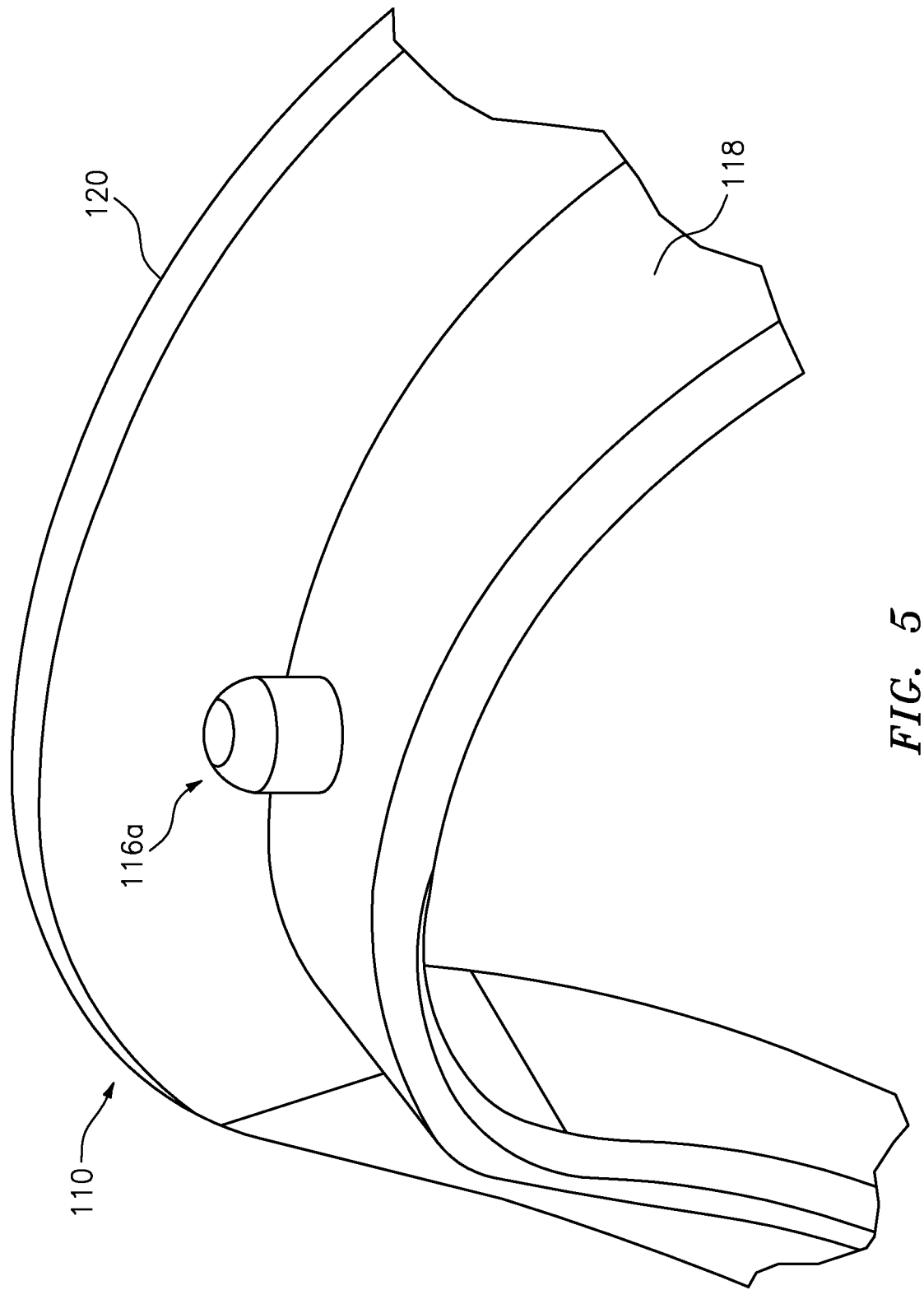
FIG. 5 is an enlarged partial view of just an upper portion of the front rim.
Figure 6:
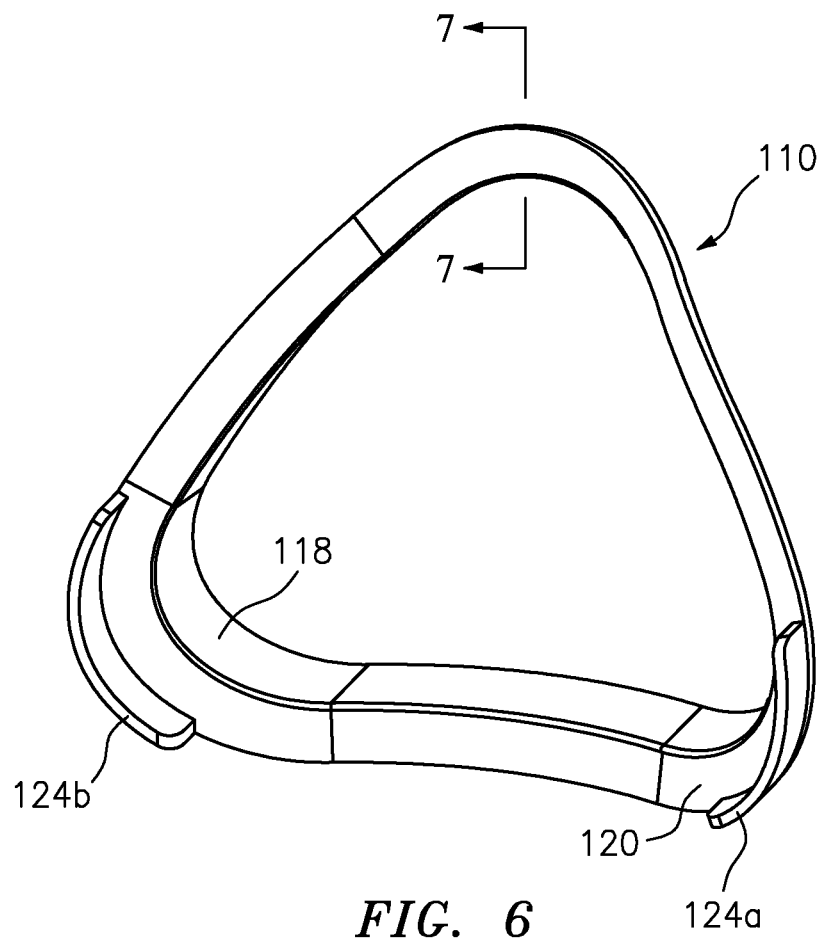
FIG. 6 is a perspective view of the rear of the cushion frame.
Figure 7:
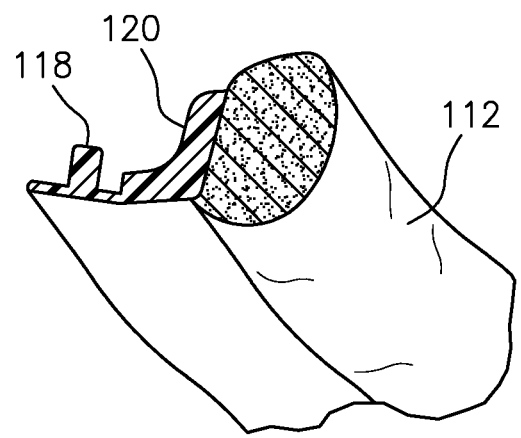
FIG. 7 is a cross-sectional view of the cushion frame with an attached cushion.
Figure 8:
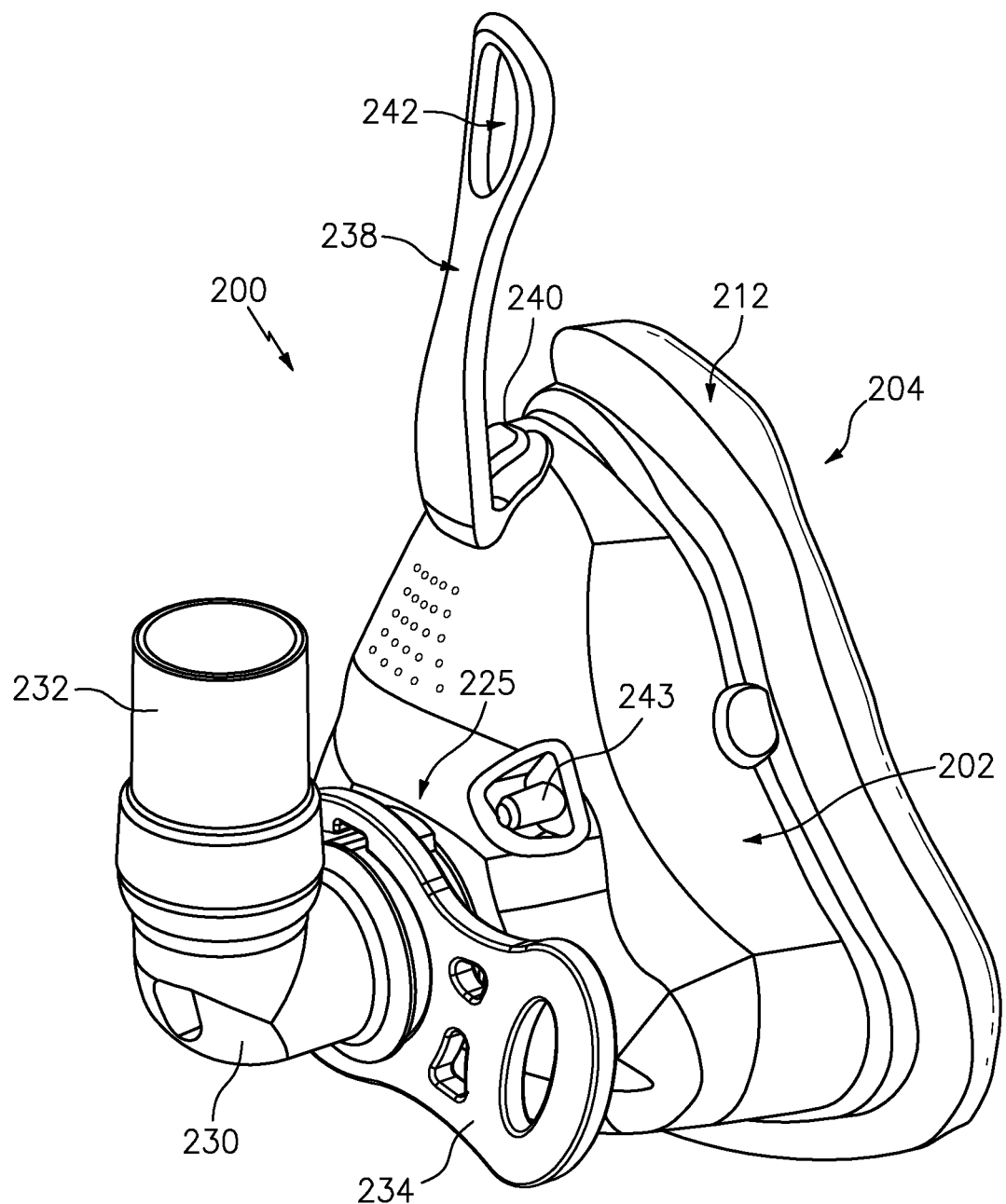
FIG. 8 is a perspective view of another preferred full-face CPAP mask embodiment with a replaceable cushion frame (with an affixed cushion) removably attached to the frame—this time the shell has the prongs and the cushion frame has the notches.
Figure 9:
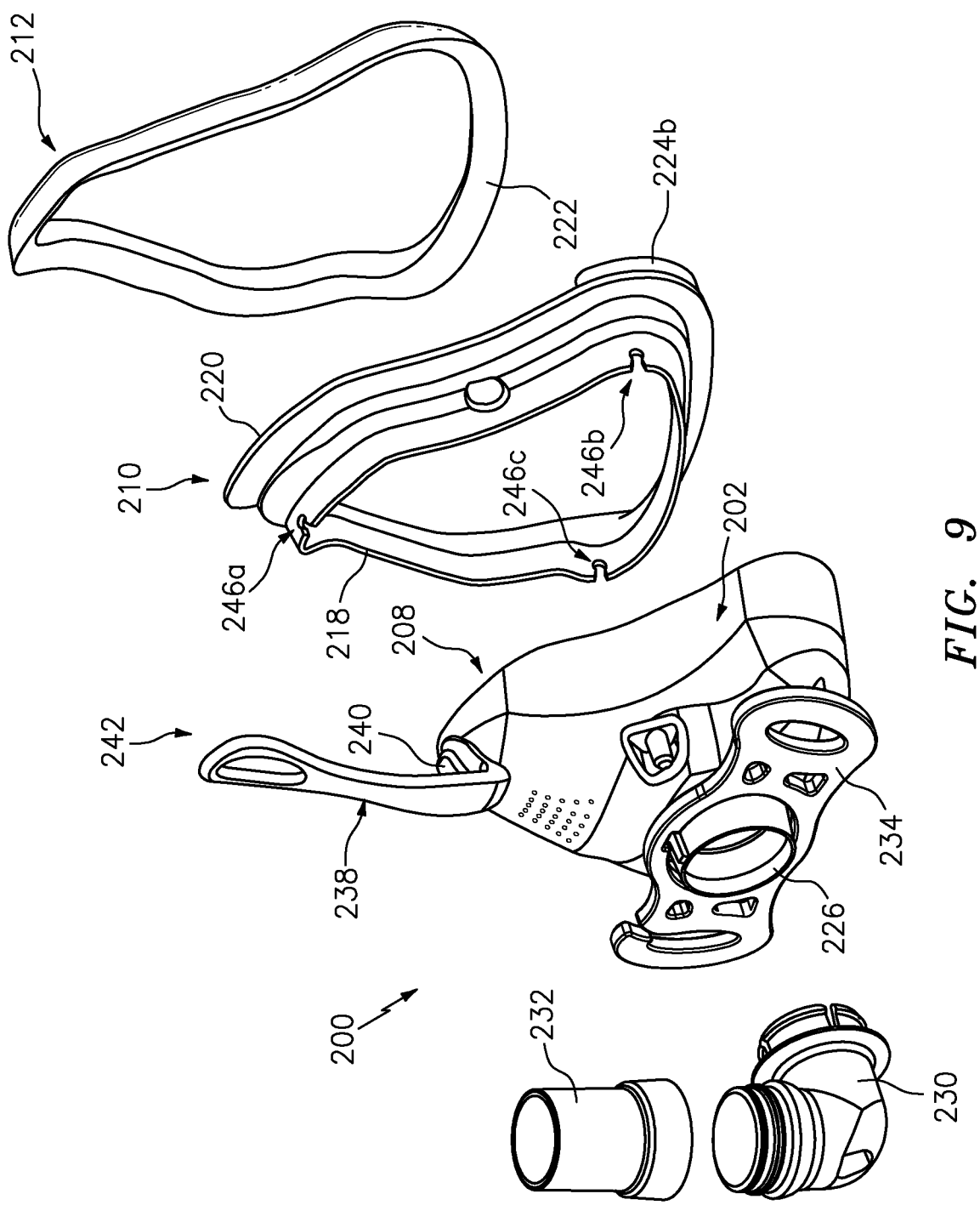
FIG. 9 is a partially exploded perspective view of the FIG. 8 mask showing (among other parts): the mask shell; a replaceable cushion frame; and a cushion.
Figure 10:
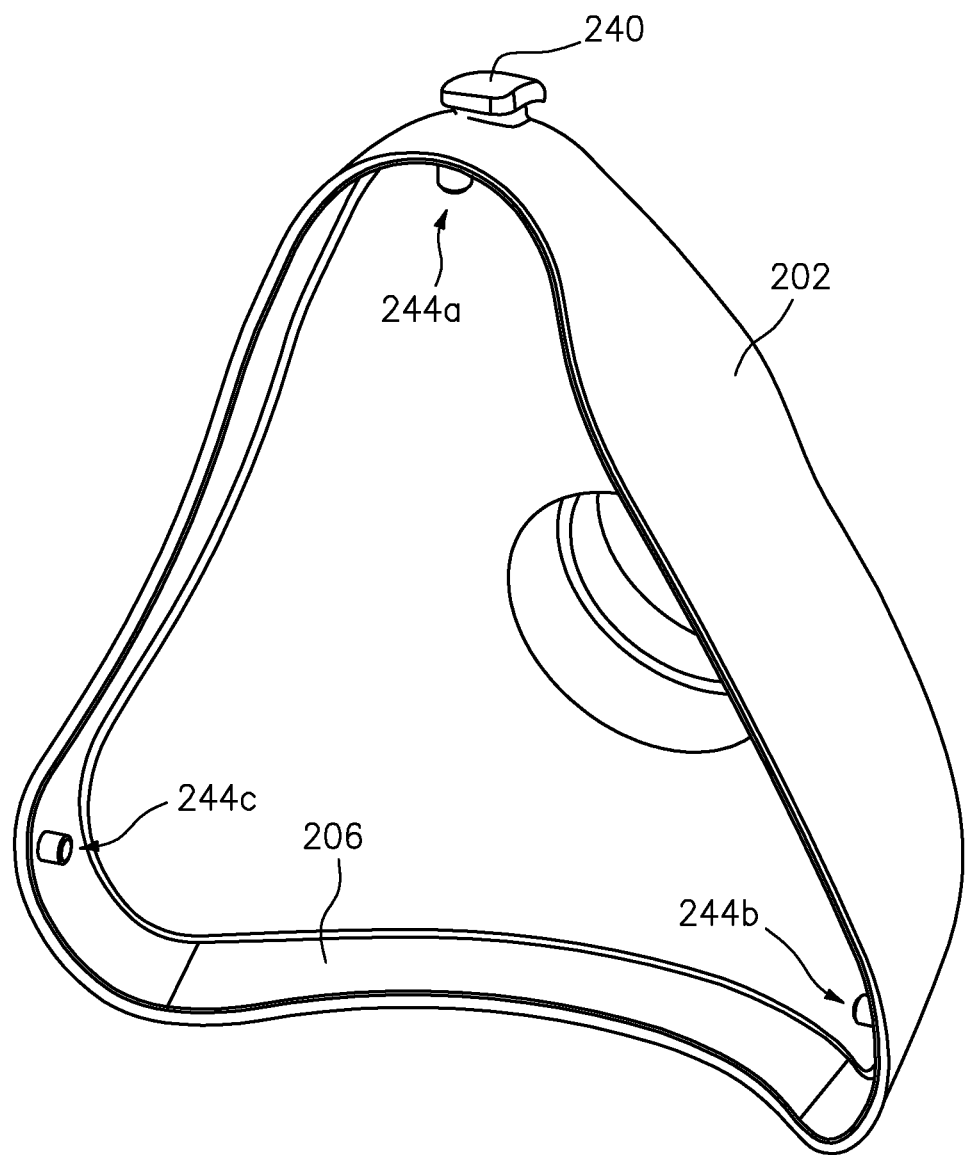
FIG. 10 is a rear perspective view of a CPAP mask shell showing: three spaced prongs extending inside the shell; and a gasket inside the shell, adjacent its opening and the prongs.
Figure 11:
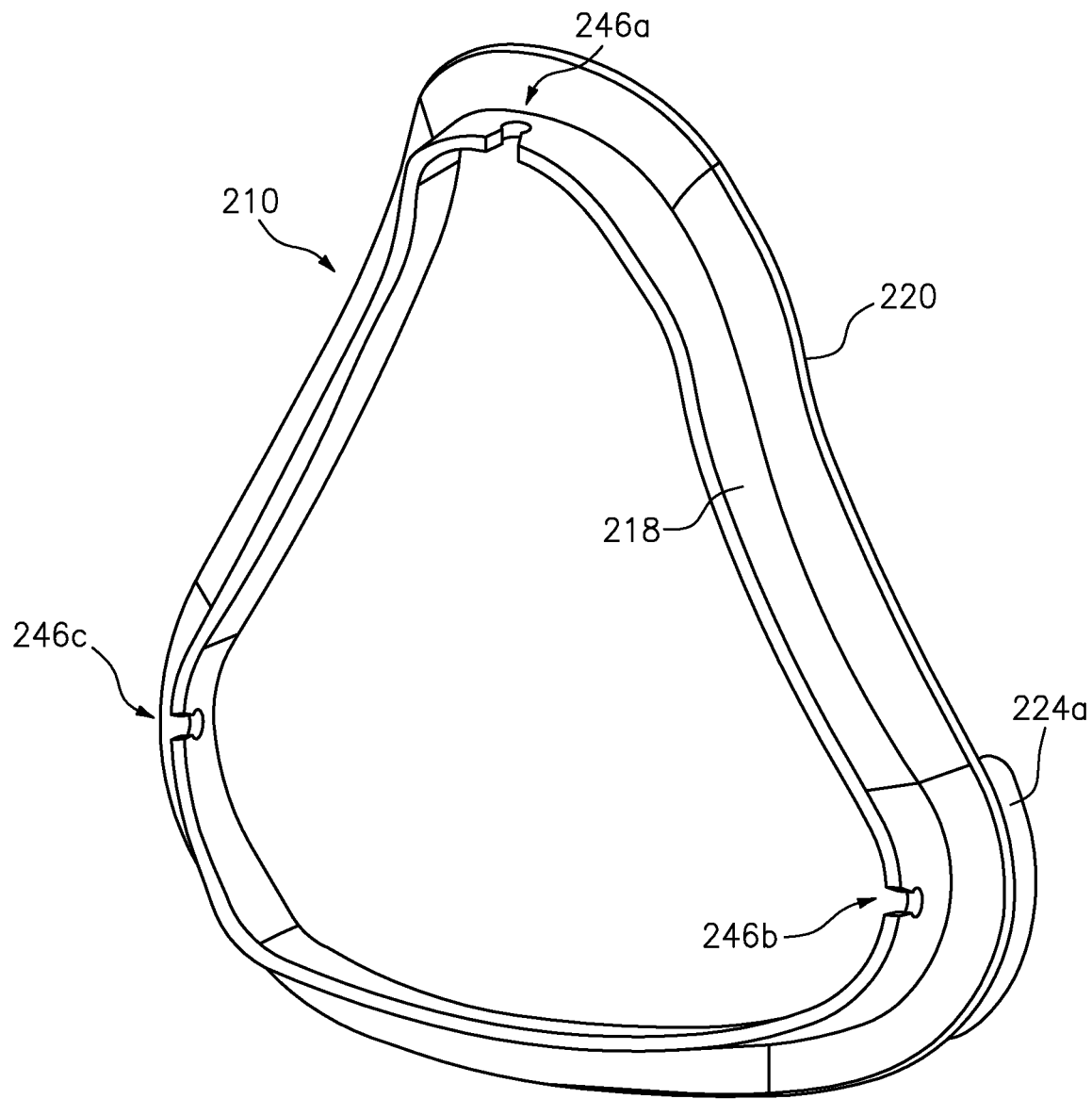
FIG. 11 is a front perspective view of the cushion frame showing three spaced notches in a rim of the frame.
Figure 12:
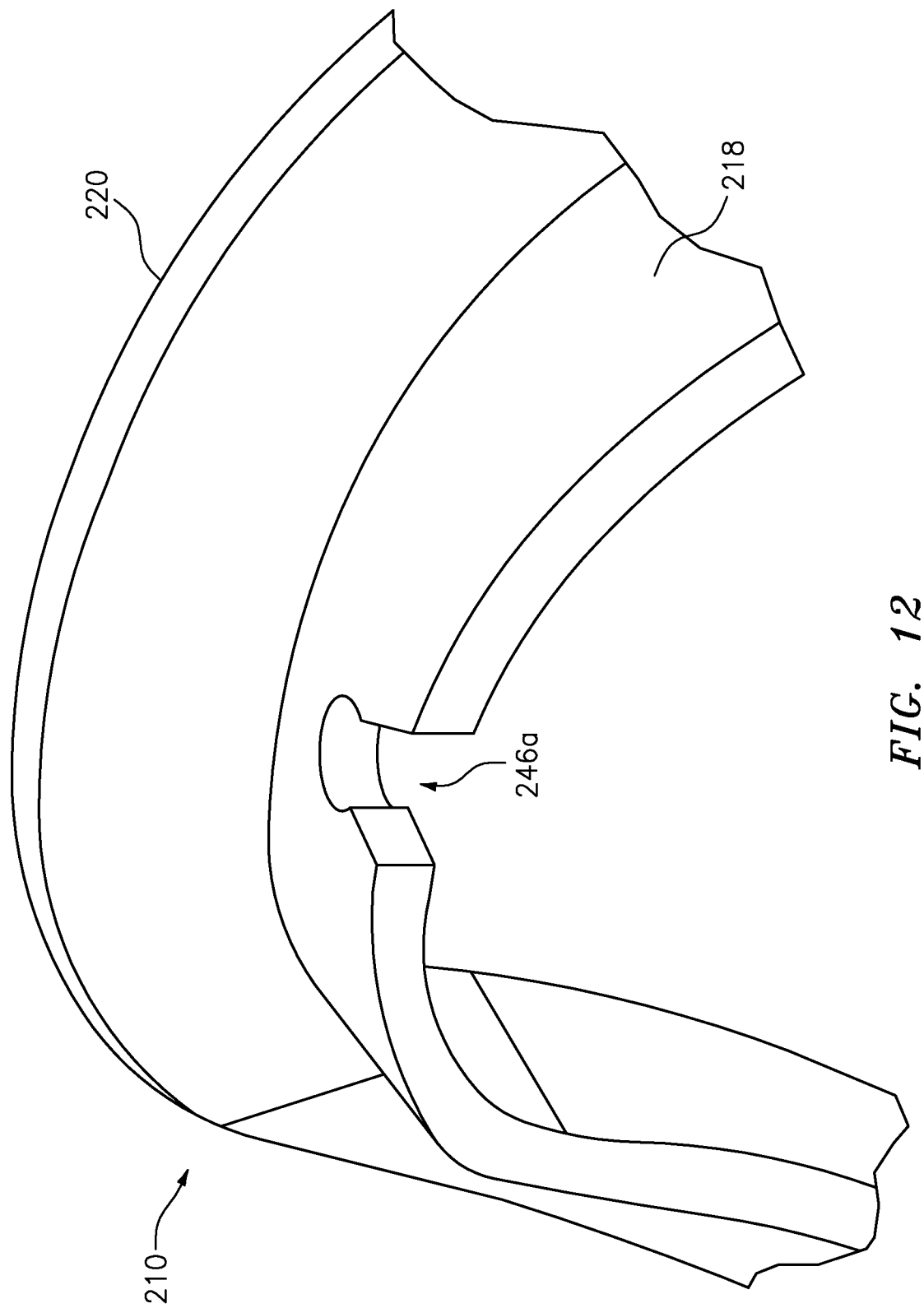
FIG. 12 is an enlarged partial view of just an upper portion of FIG. 11.

Guide prong 116a of the cushion frame 110 can be seen best in FIGS. 4 and 5. FIG. 4 shows the guide prong 116a in relation to the other relevant geometry of the cushion frame 110 and the front rim 118. FIG. 1 shows how the guide prongs 116a, 116b, 116c attach securely into the receiving notches 114a, 114b, 114c.

When the mask 104 is assembled (see FIG. 1), the gasket 106 is compressed against the rim 118 of mask shell 102. This compression helps ensure the patient or end user (not shown) will receive adequately pressurized airflow (from, e.g., a CPAP machine) without any leaks between the mask shell 102 and the replaceable frame 110.

Though not forming part of this invention: a stub shaft 126 is attached to, and extends from, the front 128 of mask shell 102; an elbow tube 130 is attached to, and swivels within, the front of the stub shaft 126; a stub tube 132 is attached to elbow tube 130; an articulating headgear connector 134—designed to be attached to lower headgear straps (not shown)—rides on a T-shaped nib 125, located atop stub shaft 126; and a top arm 138—designed to be attached to upper headgear straps (not shown)—extends upwardly near the top of the front of mask 102. See FIGS. 1-2.

The articulating headgear connector 134 and T-shaped nib 125 are constructed in accordance with U.S. Published patent application Ser. No. 13/714,881, Publication No. 20130276790 A1, entitled "ARTICULATING HEADGEAR CONNECTOR FOR RESPIRATORY MASKS". Applicant hereby incorporates by reference U.S. Published patent application Ser. No. 13/714,881, Publication No. 20130276790 A1, in its entirety.

Top arm 138 has a canted split (not shown) base which snaps onto knob 140 extending from the mask shell 102. See FIG. 1. Knob 140 is best shown in FIG. 3.

Top arm 138 has a slot 142 for receiving two upper straps of the headgear (not shown). Top arm 138 is offset. That keeps the top arm 138 and upper straps away from the wearer's forehead (not shown). That adds comfort and provides a more secure fit.

Applicant's manner of removably press-fitting the cushion frame 110 into the back 108 of the mask shell 102 can be thought of as a means comprising: the gasket 106 encircling the inside of the mask shell 102, adjacent the shell back 108; the cushion frame 110 has a rim 118, correspondingly shaped like the inside of mask shell 102 (near back 108), designed to fit snugly within the gasket 106; a plurality of spaced apart prongs 116a, 116b, 116c extending from the cushion frame 110, adjacent the rim 118; and a plurality of notches in the shell 102, correspondingly shaped like the prongs 116a, 116b, 116c, designed to receive the prongs.

Figure 19:
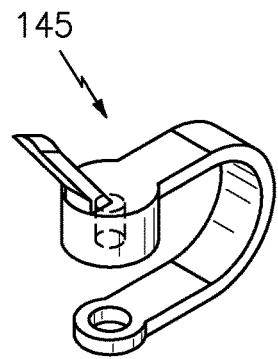
FIG. 19 discloses a cap for an anti-asphyxiation valve best show in FIGS. 1 and 8.

FIG. 19 discloses a standard plastic cap 145 for capping an anti-asphyxiation valve 143 best shown in FIG. 1. The cap 145 has a looped end which fits over a stem of an anti-asphyxiation valve 143 to prevent the cap from being lost. Similarly, such a cap is used for the anti-asphyxiation valve 243 best shown in FIG. 8.

FIGS. 8-12 show an alternate, preferred, full-face embodiment 200 in which all the parts from embodiment 100 are the same except: three prongs 244a, 244b, 244c extend inside the mask shell 202, instead of on the cushion frame 210; and three corresponding notches 246a, 246b, 246c are in the cushion frame 210 rather than the mask shell 202.

Like parts in FIGS. 8-12 (compared to their counterparts in FIGS. 1-7) are designated by the "prefix" 200 rather than the prefix 100. For example, the mask shell 102 is designated as 202 in FIGS. 8-12.

Figure 13:
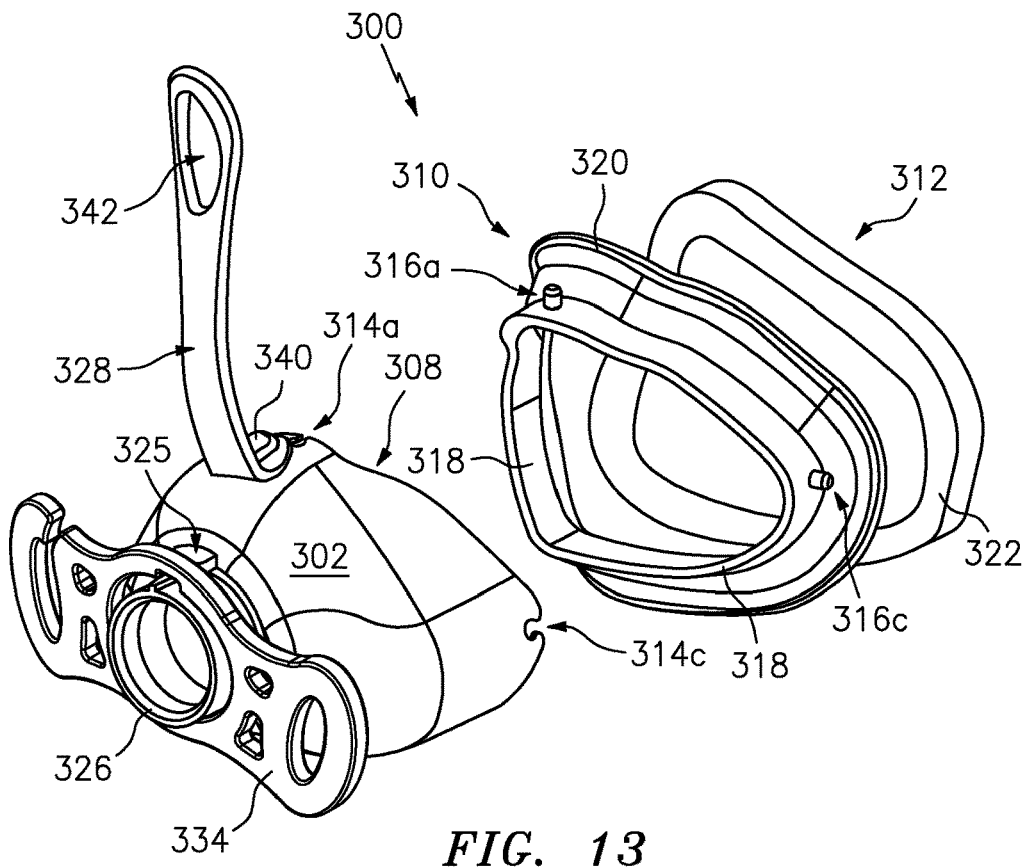
FIG. 13 is a partially exploded view of a preferred nasal mask embodiment, constructed in accordance with the present invention, showing (among other parts): a nasal mask shell with notches; a cushion frame, with prongs extending from a front rim, designed to be removably attached to the shell; and a cushion designed to be affixed to the frame.
Figure 14:
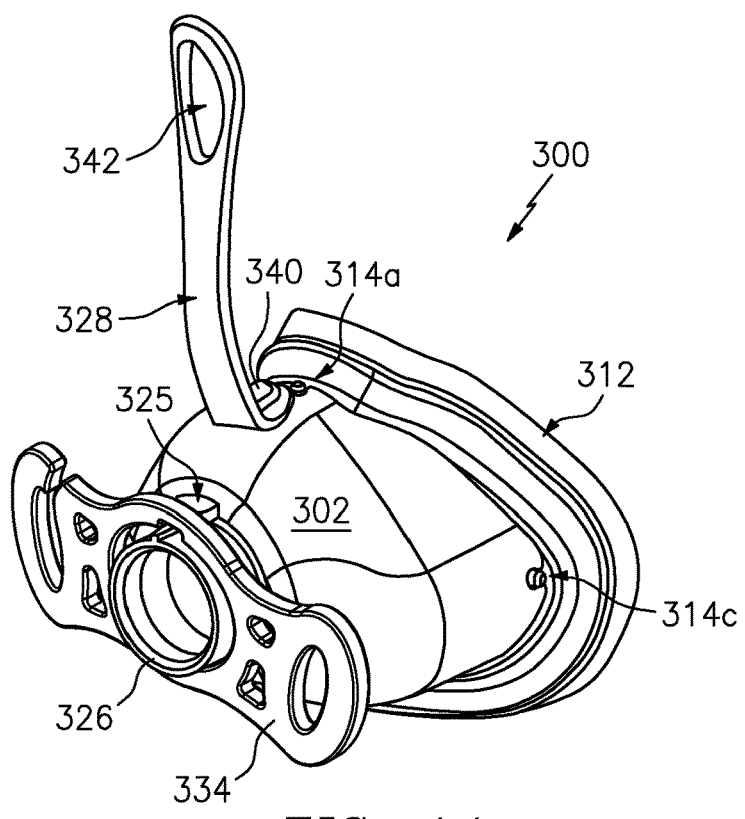
FIG. 14 is a perspective view of the FIG. 13 parts assembled.

FIGS. 13-14 show a nasal mask embodiment 300 of Applicant's invention—namely, a removable/replaceable cushion frame 310 mounted on a nasal mask 302. This nasal mask embodiment 300 shows similar parts as in the full-face mask embodiments 100, only downsized and sometimes differently shaped. Similar parts in embodiment 300 use the prefix 300 rather than the prefix 100. For example, the cushion frame 110 in FIGS. 1-7 is 310 in FIGS. 13-14.

The nasal mask embodiment 300 derives its function from the characteristics of the full-face mask embodiments 100, 200, featuring: a gel cushion 310 affixed (e.g., by glue) onto a rim 312 of the replaceable cushion frame 310; three locating prongs 316a, 316b, 316c) on the cushion frame 310; corresponding locating notches (two shown at 314a, 314c) in the receiving shell 302; and a gasket 306 attached to the rim 312.

There is a gasket 306 (not shown) encircling and fused to the inside of shell 302; and a cushion frame 310 (see FIG. 13), with an integrally attached cushion 312 inside (see FIG. 14), removably mounted inside shell 302 (see FIG. 14) and against gasket 306.

As in embodiment 100, guide prongs 316a, 316b, 316c snap into notches 314a, 314b, 314c (both sets spaced around the shell) to secure the cushion frame 310 (and its permanently attached cushion 310) to the mask shell 302. The rim 318 on the cushion frame 310 fits into shell 302, where the rim 318 seals against gasket 308.

Figure 15:
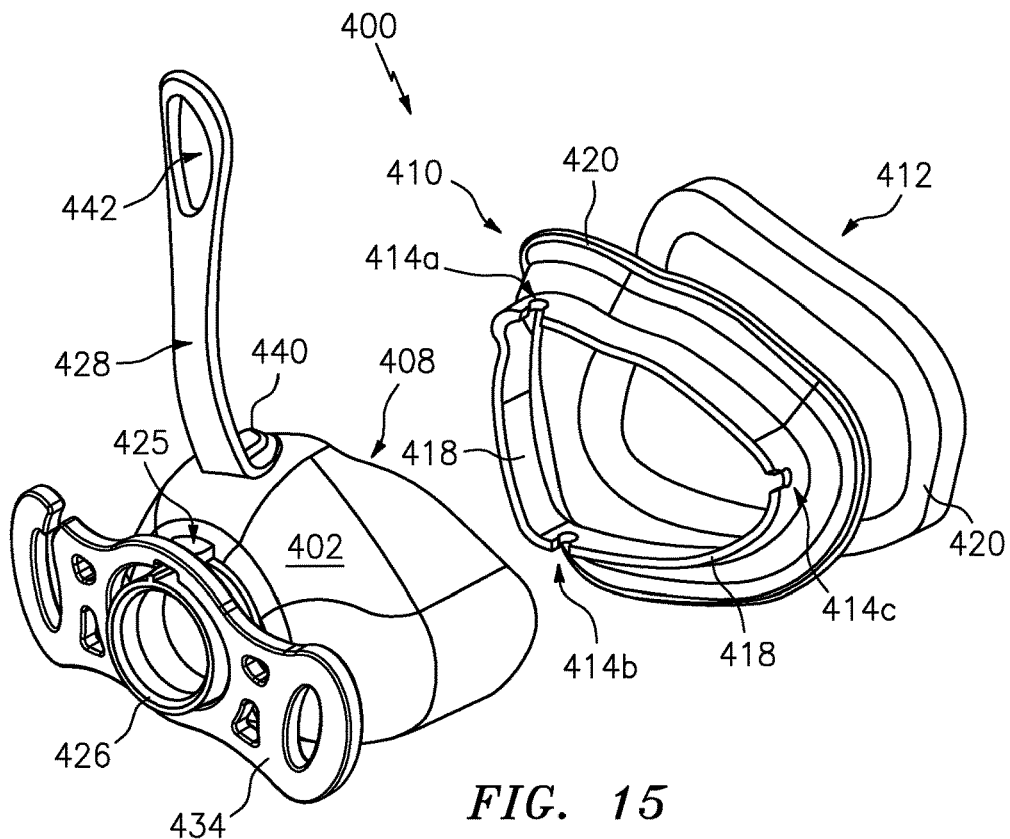
FIG. 15 is a partially exploded view of an alternately preferred nasal mask embodiment showing (among other parts): a nasal mask shell with prongs extending inside the shell; a cushion frame, with notches in a front rim, designed to be removably attached to the shell; and a cushion designed to be affixed to the frame.
Figure 16:
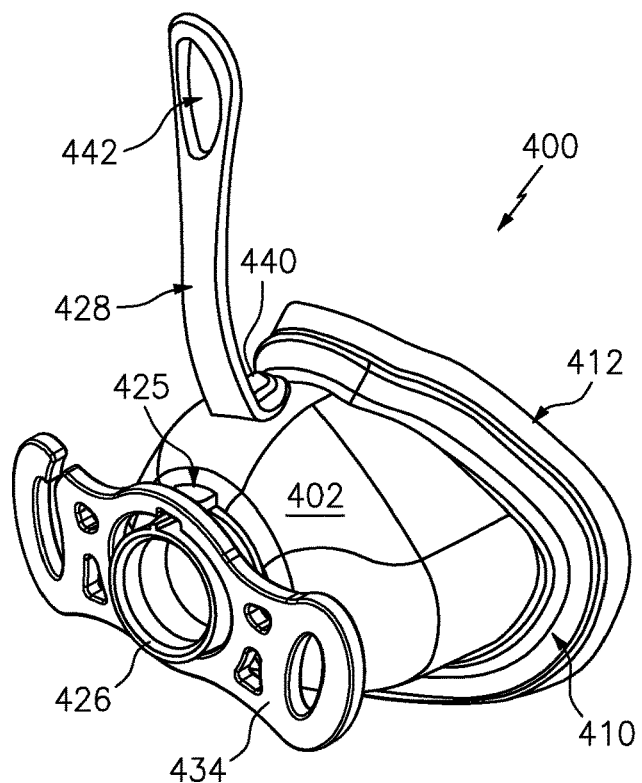
FIG. 16 is a perspective view of the FIG. 15 parts assembled.

Like parts in FIGS. 15-16 (compared to their counterparts in FIGS. 13-14) are designated by the "prefix" 400 rather than the prefix 300. For example, the mask shell 302 is designated as 402 in FIGS. 15-16.

FIGS. 15-16 show an alternate, preferred, nasal embodiment 400 in which all the parts from embodiment 300 are the same except: three prongs (not shown, but like 244a, 244b, 244c) extend inside the mask shell 402 rather than on the cushion frame 410; and three corresponding notches 414a, 414b, 414c are in the cushion frame 410 rather than the mask shell 402.

The present invention provides for a replaceable cushion for a respiratory mask (e.g., a CPAP mask) which exhibits improvements in ease of use, cleaning, reliability, and comfort for an end-user. The receiving notches of the mask interlock with the guide prongs of the cushion frame to provide for simplified assembly and disassembly which in turn improves patient compliance.

This system allows for different sized cushions, such as small, medium and large, to be provided to an end user with a single mask shell. That ensures the end user does not have to buy multiple masks before finding the right fit.

Figure 17C:
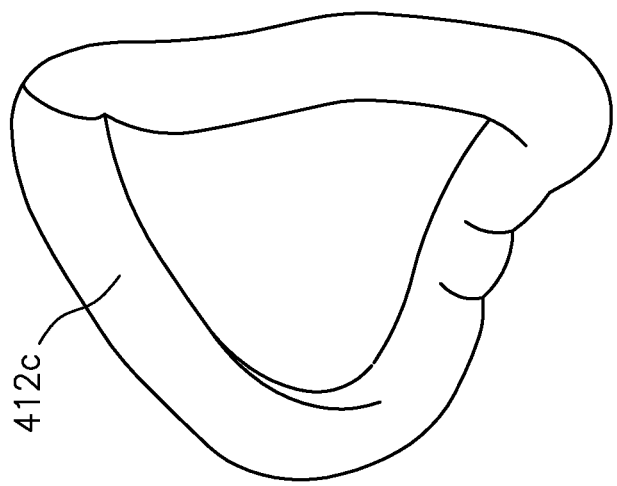
FIGS. 17*a*, 17*b*, 17*c* are perspective views of three differently sized cushions, attached to similar cushion frames, for a nasal mask.
Figure 17B:
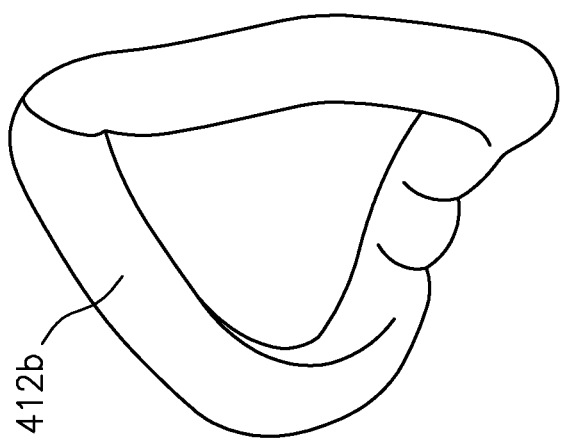
Figure 17A:
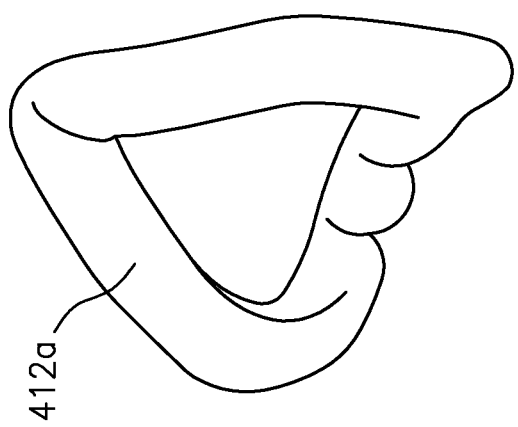
Figure 18A:
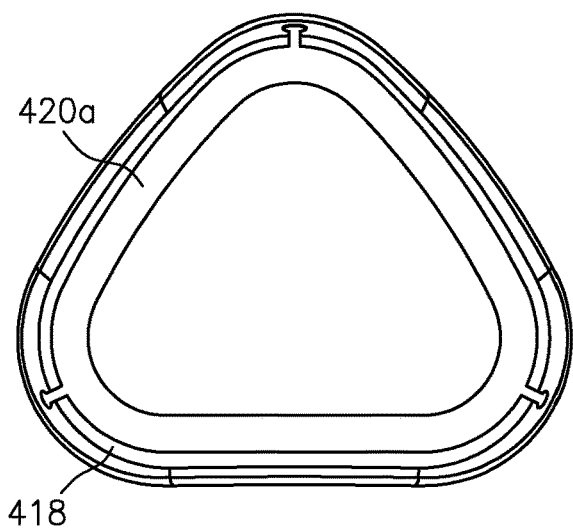
FIGS. 18*a*, 18*b*, 18*c* are plan views of an identical front rim attached to three differently sized flat lips at shifted locations.
Figure 18B:
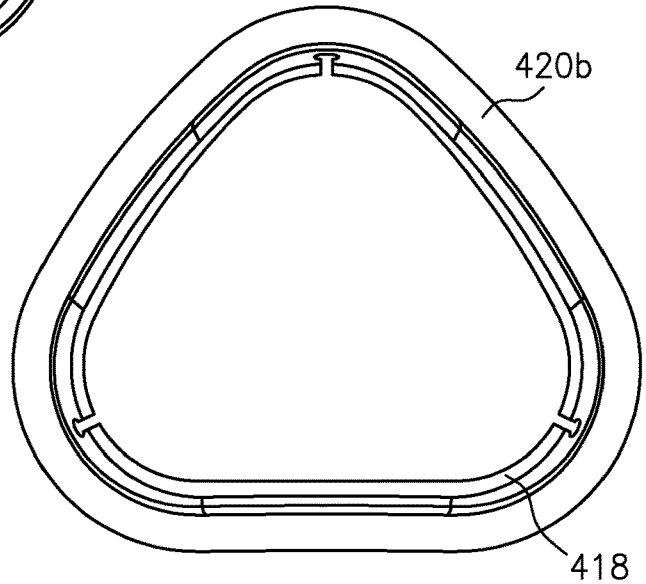
Figure 18C:
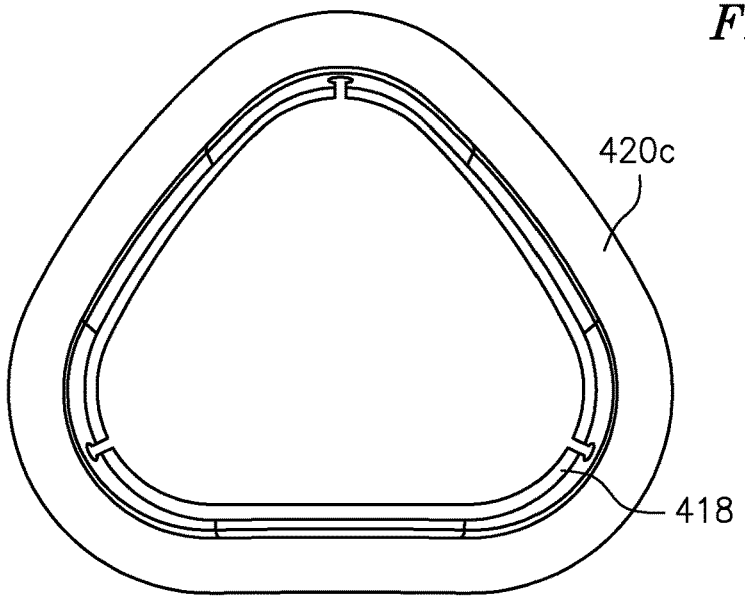

FIGS. 17a, 17b, 17c illustrates three differently sized cushions—small 412a, medium 412b and large 412c to accommodate different widths noses/nares—attached to differently sized flat lips 420a, 420b, 420c (see FIGS. 18a, 18b, 18c). Each frame lip 420a, 420b, 420c is attached to a single sized and shaped rim 418a, 418b, 418c (see FIGS. 18a, 18b, 18c); this allows each cushion frame 410a, 410b, 410c to be press-fit into a single mask shell (e.g., 402).

Cushions 412a, 412b, 412c, preferably gel- or saline-filled bladders, have the same thickness. Medium cushion 412a is otherwise proportionally larger than smaller cushion 412a; and larger cushion 412c is otherwise proportionally larger than mid-size (medium) cushion 412b. Medium cushion 412b has a bigger hole than smaller cushion 412a to accommodate a wider nose with a larger space between the nares; and the largest cushion 412c has an even wider hole.

To accommodate the differently sized cushions 412a, 412b, 412c and holes: the flat lips 420a, 420b, 420c of cushion frames 410a, 410b, 410c are attached to rims 418a, 418b, 418c at different locations. See FIGS. 18a, 18b, 18c.

As mentioned in the Background section, CPAP masks have to be regularly cleaned. By allowing for quick disassembly, this invention allows the cushion frames 110, 210, 310, 410 (and affixed gel cushions 112, 212, 312, 412) to be removed off the mask shells 102, 202, 302, 402. Then the gel cushions 112, 212, 312, 412 can be easily cleaned and reattached, by the cushion frames 110, 210, 310, 410 to the shells 102, 202, 302, 402.

In all the illustrated mask embodiments 100, 200, 300, 400, the cushion frame assemblies (i.e., the cushion frames 110, 210, 310, 410 and attached cushions 112, 212, 312, 412) are press-fit respectively into the mask shells 102, 202, 302, 402. The prongs and notches not only help keep the parts together, but in addition they also act as locators to ensure each cushion is properly aligned in the mask shell.

Though not shown, the replaceable cushion could be used on a textile nasal mask. Like the embodiments 300, 400 the textile mask would feature: a replaceable cushion/frame assembly having a gel cushion and an integrally attached cushion frame; locating prongs on the cushion frame, locating notches (or the like) in the receiving shell; a gasket on the receiving shell; and a textile mask body fused to the receiving shell.

In all the illustrated mask embodiments 100, 200, 300, 400, the gaskets 106, 206, 306, 406 are located inside the mask shells 102, 202, 302, 402. Alternatively, the gaskets could be located on the rims 118, 218, 318, 418 of the cushion frames 110, 210, 310, 410.

Applicant's invention can be thought of broadly as a method comprising:
a. providing a respiratory (e.g., CPAP) mask shell with a gasket inside the shell, adjacent a back of the shell;
b. providing a plurality of differently shaped cushions respectively affixed to cushion frames, wherein each of the frames has a rim correspondingly shaped like the end portion of the shell;
c. removably press-fitting the cushion frames, at separate times, into the shell and within the gasket, until a proper fitting cushion is obtained; and
d. whereby a customer does not have to purchase multiple respiratory masks before obtaining a proper fitting cushion.

The method can include additional alternative limitations:
a. inserting spaced apart prongs, which extend into the mask shell, into correspondingly shaped notches of a cushion frame, as the rim of the cushion frame is press-fit into the shell and the gasket; or
b. inserting spaced apart prongs, extending from the rim, into correspondingly shaped notches of the mask shell, as the rim of a cushion frame is press-fit into the shell and the gasket.

It should be understood that obvious structural modifications can be made without departing from the spirit of the invention. Accordingly, reference should be made primarily to the accompanying claims rather than the foregoing description to determine the scope of the invention.

I claim:

1. An apparatus comprising:
a. a respiratory mask shell having a front and a back, the back comprising an inside perimeter and an inside surface, wherein the respiratory mask shell further has a prong extended from the inside surface; and
b. a cushion frame comprising a rim and an annular flat lip, wherein the annular flat lip has a cushion affixed thereto, the annular flat lip extends substantially perpendicular to the rim, and the rim has a shape corresponding to the inside perimeter of the back of the respiratory mask shell,
wherein the rim is configured to be directly friction-fit against the inside perimeter of the back of the respiratory mask shell, the direct friction-fit creating an airtight seal between the rim and the respiratory mask shell,
wherein the entirety of the cushion is spaced apart from the respiratory mask shell when the rim is directly friction-fit against the inside perimeter of the back of the respiratory mask shell,
wherein the rim has a notch located in a front perimeter edge thereof,
wherein the notch extends in a direction towards the annular flat lip,
wherein the notch of the rim is configured to receive the prong of the respiratory mask shell when the rim is directly friction-fit against the inside perimeter of the back of the respiratory mask shell.

2. The apparatus of claim 1, wherein the respiratory mask shell is a continuous positive airway pressure (CPAP) mask.

3. The apparatus of claim 1, wherein the respiratory mask shell comprises a gasket coupled to and positioned along the inside perimeter of the back of the respiratory mask shell, wherein the rim is configured to be directly friction-fit against the gasket.

4. The apparatus of claim 3, wherein the direct friction-fit of the rim against the gasket causes compression of the gasket, compression of the gasket causing the airtight seal.

5. The apparatus of claim 3, wherein the gasket is made of at least one of a thermoplastic elastomer or a thermoplastic polyurethane.

6. The apparatus of claim 3, wherein the gasket is fused to the inside perimeter of the back of the respiratory mask shell.

7. The apparatus of claim 1, wherein:
the notch is formed as a concave depression within the front perimeter edge of the rim; and
the direct friction-fit of the rim against the inside perimeter comprises moving the prong toward a concave surface of the notch.

8. The apparatus of claim 1, wherein the cushion frame is affixed to an outside surface of the cushion.

9. A method comprising:
a. providing a respiratory mask shell having a front and a back, the back comprising an inside perimeter and an inside surface, wherein the respiratory mask shell further has a prong extending from the inside surface; and
b. providing a first cushion frame comprising a first rim and an annular flat lip, wherein the annular flat lip has a first cushion affixed thereto, the annular flat lip extends substantially perpendicular to the first rim, and the first rim has a shape corresponding to the inside perimeter of the back of the respiratory mask shell, the first rim being configured to be directly friction-fit against the inside perimeter of the back of the respiratory mask shell, the direct friction-fit creating an airtight seal between the first rim and the respiratory mask shell, the entirety of the first cushion being spaced apart from the respiratory mask shell when the first rim is directly friction-fit against the inside perimeter of the back of the respiratory mask shell, wherein the first rim has a notch located in a front perimeter edge thereof, wherein the notch extends in a direction towards the annular flat lip, and wherein the notch of the first rim is configured to receive the prong of the respiratory mask shell when the first rim is directly friction-fit against the inside perimeter of the back of the respiratory mask shell.

10. The method of claim 9, wherein providing the respiratory mask shell comprises:
providing the respiratory mask shell with a gasket coupled to and positioned along the inside perimeter of the back of the respiratory mask shell, wherein the first rim is configured to be directly friction-fit against the gasket.

11. The method of claim 10, wherein providing the first cushion frame comprises:
providing the first cushion frame such that the direct friction-fit of the first rim against the gasket causes compression of the gasket, compression of the gasket causing the airtight seal.

12. The method of claim 9, wherein providing the first cushion frame comprises:
providing the first cushion frame with the notch formed as a concave depression within the front perimeter edge of the first rim, wherein the direct friction-fit of the first rim against the inside perimeter comprises moving the prong toward a concave surface of the notch.

13. The method of claim 9, wherein:
providing the first cushion frame comprises providing the first cushion frame with the first rim having a prong extending from an outside surface of the first rim; and
providing the respiratory mask shell comprises providing the respiratory mask shell with a notch located in a perimeter edge of the back of the respiratory mask shell, the notch of the respiratory mask shell configured to receive the prong of the first rim when the first rim is directly friction-fit against the inside perimeter of the back of the respiratory mask shell.

14. The method of claim 13, wherein providing the respiratory mask shell comprises:
providing the respiratory mask shell with the notch formed as a concave depression within an edge of the back of the respiratory mask shell, wherein the direct friction-fit of the first rim against the inside perimeter comprises moving the prong of the first rim toward a concave surface of the notch of the respiratory mask shell.

15. The method of claim 9, further comprising:
c. providing a second cushion frame having a second cushion affixed thereto, the second cushion having at least one dimension different from that of the first cushion, the second cushion frame comprising a second rim having the shape corresponding to the inside perimeter of the back of the respiratory mask shell, the second rim being configured to be directly friction-fit against the inside perimeter of the back of the respiratory mask shell.

16. An apparatus comprising:
a. a respiratory mask shell having a front and a back, the back comprising an inside perimeter and a perimeter edge, wherein the respiratory mask shell further has a notch located in a perimeter edge of the back of the respiratory mask shell; and
b. a cushion frame comprising a rim, an opening to receive pressurized airflow, and an annular flat lip, wherein the annular flat lip has a cushion affixed thereto, the annular flat lip extends substantially perpendicular to the rim, and the rim has a shape corresponding to the inside perimeter of the back of the respiratory mask shell,
wherein the rim is configured to be directly friction-fit against the inside perimeter of the back of the respiratory mask shell, the direct friction-fit creating an airtight seal between the rim and the respiratory mask shell,
wherein the entirety of the cushion is spaced apart from the respiratory mask shell when the rim is directly friction-fit against the inside perimeter of the back of the respiratory mask shell,
wherein the rim comprises a prong extending from an outside surface of the rim,
wherein the outside surface is disposed opposite to the opening of the cushion frame,
wherein the notch of the respiratory mask shell is configured to receive the prong of the rim when the rim is directly friction-fit against the inside perimeter of the back of the respiratory mask shell.

17. The apparatus of claim 16, wherein the respiratory mask shell is a continuous positive airway pressure (CPAP) mask.

18. The apparatus of claim 16, wherein the respiratory mask shell comprises a gasket coupled to and positioned along the inside perimeter of the back of the respiratory mask shell, wherein the rim is configured to be directly friction-fit against the gasket.

19. The apparatus of claim 18, wherein the direct friction-fit of the rim against the gasket causes compression of the gasket, compression of the gasket causing the airtight seal.

20. The apparatus of claim 18, wherein the gasket is made of at least one of a thermoplastic elastomer or a thermoplastic polyurethane.

21. The apparatus of claim 18, wherein the gasket is fused to the inside perimeter of the back of the respiratory mask shell.

22. The apparatus of claim 16, wherein:
the notch is formed as a concave depression within the perimeter edge of the back of the respiratory mask shell; and
the direct friction-fit of the rim against the inside perimeter comprises moving the prong toward a concave surface of the notch.

23. The apparatus of claim 16, wherein the cushion frame is affixed to an outside surface of the cushion.

24. A method comprising:
a. providing a respiratory mask shell having a front and a back, the back comprising an inside perimeter and a perimeter edge, wherein the respiratory mask shell further has a notch located in a perimeter edge of the back of the respiratory mask shell; and
b. providing a first cushion frame comprising a first rim, an opening to receive pressurized airflow, and an annular flat lip, wherein the annular flat lip has a first cushion affixed thereto, the annular flat lip extends substantially perpendicular to the first rim, and the first rim has a shape corresponding to the inside perimeter of the back of the respiratory mask shell, the first rim being configured to be directly friction-fit against the inside perimeter of the back of the respiratory mask shell, the direct friction-fit creating an airtight seal between the first rim and the respiratory mask shell, the entirety of the first cushion being spaced apart from the respiratory mask shell when the first rim is directly friction-fit against the inside perimeter of the back of the respiratory mask shell, wherein the first rim comprises a prong extending from an outside surface of the first rim, wherein the outside surface is disposed opposite to the opening of the first cushion frame, and wherein the notch of the respiratory mask shell is configured to receive the prong of the first rim when the first rim is directly friction-fit against the inside perimeter of the back of the respiratory mask shell.

25. The method of claim 24, wherein providing the respiratory mask shell comprises:
providing the respiratory mask shell with a gasket coupled to and positioned along the inside perimeter of the back of the respiratory mask shell, wherein the first rim is configured to be directly friction-fit against the gasket.

26. The method of claim 25, wherein providing the first cushion frame comprises:
providing the first cushion frame such that the direct friction-fit of the first rim against the gasket causes compression of the gasket, compression of the gasket causing the airtight seal.

27. The method of claim 24, wherein providing the respiratory mask shell comprises:
providing the respiratory mask shell with the notch formed as a concave depression within an edge of the back of the respiratory mask shell, wherein the direct friction-fit of the first rim against the inside perimeter comprises moving the prong toward a concave surface of the notch.

28. The method of claim 24, further comprising:
c. providing a second cushion frame having a second cushion affixed thereto, the second cushion having at least one dimension different from that of the first cushion, the second cushion frame comprising a second rim having the shape corresponding to the inside perimeter of the back of the respiratory mask shell, the second rim being configured to be directly friction-fit against the inside perimeter of the back of the respiratory mask shell.

* * * * *